United States Patent
Ohyu et al.

(10) Patent No.: US 9,649,041 B2
(45) Date of Patent: May 16, 2017

(54) BLOOD FLOW PERFUSION ANALYZING APPARATUS, BLOOD FLOW PERFUSION ANALYZING METHOD, FLUID ANALYZING APPARATUS AND FLUID ANALYZING

(75) Inventors: Shigeharu Ohyu, Yaita (JP); Yasuo Sakurai, Otawara (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 804 days.

(21) Appl. No.: 12/938,578

(22) Filed: Nov. 3, 2010

(65) Prior Publication Data
US 2011/0130668 A1   Jun. 2, 2011

(30) Foreign Application Priority Data

Nov. 27, 2009   (JP) .................................. 2009-270339
Sep. 8, 2010    (JP) .................................. 2010-200436

(51) Int. Cl.
A61B 5/02      (2006.01)
A61B 5/026     (2006.01)
(Continued)

(52) U.S. Cl.
CPC ............ *A61B 5/0263* (2013.01); *A61B 5/027* (2013.01); *A61B 6/037* (2013.01); *A61B 6/481* (2013.01);
(Continued)

(58) Field of Classification Search
CPC .. G01R 33/563; G01R 33/5601; A61B 5/026; A61B 5/022; A61B 5/055; A61B 5/02416; A61B 6/481; G06T 7/0012
(Continued)

(56) References Cited

U.S. PATENT DOCUMENTS 6,809,419 B2   10/2004   Minami et al.
6,898,453 B2    5/2005   Lee
(Continued)

FOREIGN PATENT DOCUMENTS

| JP | 2004-519304 | 7/2004 |
| JP | 2007-144139 | 6/2007 |
| JP | 2007-525250 | 9/2007 |

OTHER PUBLICATIONS

Østergaard, Principles of Cerebral Perfusion Imaging by Bolus Tracking, Journal of Magnetic Resonance Imaging, vol. 22, pp. 710-717, 2005.*

(Continued)

*Primary Examiner* — Michael Kahelin
*Assistant Examiner* — Tho Tran
(74) *Attorney, Agent, or Firm* — Nixon & Vanderhye P.C.

(57) ABSTRACT

According to one embodiment, a blood flow perfusion analyzing apparatus includes tissue and arterial TCC calculation units, first and second making units, a deconvolution unit and a blood flow information calculation unit. The tissue TCC calculation unit obtains tissue TCCs. The arterial TCC calculation unit calculates an arterial TCC. The first making unit makes first sets, starting from a first time in which elements corresponding to the tissue are arrayed one-dimensionally, based on the tissue TCCs. The second making unit makes a second set, starting from a second time after the first time, in which elements corresponding to the artery are arrayed two-dimensionally, based on the arterial TCC. The deconvolution unit calculates transfer functions of the tissue based on the first and second sets. The blood flow information calculation unit calculates information on a blood flow perfusion based on the transfer functions.

15 Claims, 7 Drawing Sheets

(51) Int. Cl.
*A61B 5/027* (2006.01)
*A61B 6/00* (2006.01)
A61B 5/00 (2006.01)
A61B 6/03 (2006.01)
G01R 33/563 (2006.01)

(52) U.S. Cl.
CPC .............. *A61B 6/504* (2013.01); *A61B 6/507* (2013.01); *G01R 33/56366* (2013.01); A61B 5/7285 (2013.01); A61B 6/032 (2013.01); A61B 6/501 (2013.01); A61B 6/541 (2013.01); G01R 33/56333 (2013.01)

(58) Field of Classification Search
USPC ........ 600/507, 504, 479, 431, 420, 419, 410
See application file for complete search history.

(56) References Cited

U.S. PATENT DOCUMENTS

| | | | |
|---|---|---|---|
| 7,193,263 B2 | 3/2007 | Barth | |
| 7,199,472 B2 | 4/2007 | Minami et al. | |
| 7,512,435 B2 | 3/2009 | Wu et al. | |
| 2002/0158306 A1 | 10/2002 | Niitsu | |
| 2003/0045791 A1* | 3/2003 | Carroll | 600/419 |
| 2003/0214378 A1 | 11/2003 | Tung et al. | |
| 2006/0038257 A1 | 2/2006 | Anzai | |
| 2007/0112264 A1* | 5/2007 | Wu | A61B 5/0263 600/410 |
| 2008/0194943 A1* | 8/2008 | Lorenz et al. | 600/419 |
| 2009/0124898 A1* | 5/2009 | Stodilka et al. | 600/431 |
| 2009/0297008 A1* | 12/2009 | Taxt et al. | 382/131 |

OTHER PUBLICATIONS

Wu et al., "Tracer Arrival Timing-Insensitive Technique for Estimating Flow in MR Perfusion-Weighted Imaging Using Singular Value Decomposition With a Block-Circulant Deconvultion Matrix", *Magnetic Resonance in Medicine*, vol. 50, 2003, pp. 164-174.

Smith et al., "Removing the Effect of SVD Algorithmic Artifacts Present in Quantitative MR Perfusion Studies", *Magnetic Resonance in Medicine*, vol. 51, 2004, pp. 631-634.

Office Action issued Feb. 12, 2014, in JP Patent Application No. 2010-200436.

* cited by examiner

BLOOD FLOW PERFUSION ANALYZING APPARATUS, BLOOD FLOW PERFUSION ANALYZING METHOD, FLUID ANALYZING APPARATUS AND FLUID ANALYZING

CROSS REFERENCES TO RELATED APPLICATIONS

This application is based upon and claims the benefit of priorities from Japanese Patent Application No. 2009-270339 filed on Nov. 27, 2009 and Japanese Patent Application No. 2010-200436 filed on Sep. 8, 2010: the entire contents of Japanese Patent Application No. 2009-270339 and Japanese Patent Application No. 2010-200436 are incorporated herein by reference.

BACKGROUND

1. Field

Embodiments described herein relate generally to a blood flow perfusion analyzing apparatus, a blood flow perfusion analyzing method, a fluid analyzing apparatus and a fluid analyzing method.

2. Description of the Related Art

Conventionally, an examination in which contrast medium is injected from a vein, time series image data is acquired and the image data is analyzed to obtain information on a blood flow perfusion in tissue is performed with an X-ray CT (Computed Tomography) apparatus or an MRI (Magnetic Resonance Imaging) apparatus. This examination is called perfusion examination using the fact that a degree of concentration of contrast medium in an imaging section can be acquired as concentration changes in an image.

For example, a TCC, (Time Concentration Curve) corresponding to arterial blood flowing into tissue is set to an input function $a_i$, deconvolution of the input function with a measured TCC $C_i$ of the tissue is performed, an impulse response function (residue function) $R_i$ inherent in the tissue is calculated and parameters including a blood flow (CBF: Cerebral Blood Flow in case of a brain) which is an index representing a blood flow perfusion quantitatively a MTT (Mean Transit Time) and a blood volume (CBV: Cerebral Blood Volume in case of a brain) based on the calculated impulse response function in order to reduce a fluctuation in a pulmonary circulation and a contrast medium infection. This analysis method is called a deconvolution method.

Note that a TCC is a curve representing a time change of a quantity in proportion as a density of contrast medium. A time change curve of quantity in proportion as a density of contrast medium obtained based on contrast image data acquired by an X-ray CT apparatus is also referred to a TDC (Time Density Curve). However, it is indicated as a TCC here.

For example, non-patent document 1 applies standard SVD (Singular Value Decomposition) method or block circulant SVD method to the deconvolution method.

Here, the standard. SVD method will be described. First, a change in pixel value at each pixel j (position $r_j$) in acquired image data is measured to calculate a TCC $C_i(r_j)$ corresponding to a tissue. Then, a TCC $A_i$ corresponding to an artery is calculated based on the calculated tissue TCC $C_i$ as shown in following equation (1). In equation (1), i represents a phase number and $\Omega_A$ represents a set of pixels corresponding to the artery.

$$A_i = \frac{1}{n} \sum_{j \in \Omega_A} C_i(r_j) \quad (1)$$

Assuming that a tissue TCC $C_i$ is a deconvolution of an artery TCC $A_i$ and an impulse response function X, the tissue TCC $C_i$ can be expressed by a system equation as shown in following, equation (2). In equation (2), $T_R$ represents a time interval (TR: repetition time) imaging and $R_j$ represents an impulse response function.

$$C_i = \sum_{j=0}^{i} A_{i-j} T_R R_j = \sum_{j=0}^{i} A_{i-j} X_j \quad (2)$$

For example, assuming that data of L phases, which is derived by making the artery TCC $A_i$ and the tissue TCC $C_i$ discrete in the time axis direction, i.e. dividing a phase range of $i_{bs} \le i \le L-1$ into L equal intervals, is used for the analysis, the above-mentioned equation (2) becomes C=AX in the matrix form and can be expressed as shown in following equation (3). In equation (3). C is a L×1 column vector, A is a L×1 coefficient matrix and X is a L×1 column vector.

$$\begin{pmatrix} C_{i_{bs}} \\ C_{i_{bs}+1} \\ \vdots \\ C_{i_{bs}+L-1} \end{pmatrix} = \begin{pmatrix} a_{0,0} & a_{0,1} & \dots & a_{0,L-1} \\ a_{1,0} & a_{1,1} & \dots & a_{1,L-1} \\ \vdots & \vdots & & \vdots \\ a_{L-1,0} & a_{L-1,1} & \dots & a_{L-1,L-1} \end{pmatrix} \begin{pmatrix} X_0 \\ X_1 \\ \vdots \\ X_{L-1} \end{pmatrix} \quad (3)$$

In above-mentioned equation (3), $i_{bs}$ represents a phase at the head of a phase range to be analyzed and uses a phase at or before which the contrast concentrations in the artery and the tissue begin to rise. Each element value $a_{i,j}$ of the coefficient matrix is expressed by following equation (4). In equation (4) i=0, 1, ..., L−1 and j=0, 1, ..., L−1.

$$a_{i,j} = \begin{cases} 0 & \text{for } i-j < 0 \\ A_{i-j+i_{bs}} & \text{for } 0 \le i-j \le L-1 \end{cases} \quad (4)$$

Then, an approximate solution of above-mentioned equation (3) is calculated by a singular value decomposition. That is, the matrix A can be decomposed into 3 matrices as shown in following equation (5).

$$A = UDV^T \quad (5)$$

In above-mentioned equation (5), U is an orthonormal matrix having m rows and k columns, D is a diagonal matrix having k rows and k columns and V is an orthonormal matrix having n rows and k columns. When U, D and V are applied to above mentioned equation (3), m=n=k=L. A diagonal matrix is a matrix of which all elements other than diagonal elements are zero and an orthonormal matrix is a diagonal matrix of which diagonal elements are 1.

Assuming that $U=(u_1, u_2, \dots, u_k)$, $V=(v_1, v_2, \dots, v_k)$ and $D=\text{diag}(w_0, w_1, \dots, w_k)$, $w_k$ is sorted in descending order and subsequently $u_k$ and $v_k$ are also respectively sorted in the order corresponding to the order of the sorted $w_k$. Then, the minimum normed estimated value which is the minimum square solution of X can be calculated with the result of the singular value decomposition of the matrix A by following equation (6).

$$\tilde{X} = VWU^T C \quad (6)$$

In above mentioned equation (6), W is a diagonal matrix consisting of the reciprocals of the diagonal elements (the singular values) of D and $W = \text{diag}(1/w_0, 1/w_1, \ldots, 1/w_{G-1}, 0, 0, \ldots)$. When a singular value is below the maximum singular value times $P_{svd}$, not the reciprocal of the singular value but zero is set as a diagonal element. Therefore, W has G diagonal elements which are not zero. $P_{svd}$ is a parameter which influences strength of the regularization. When $P_{svd}$ is larger, a stronger regularization is performed.

Then, calculating the nonmed estimated value makes it possible to calculate the impulse response function $R_j$ as shown in following equation (7).

$$R_j = \tilde{X}_j / T_R \quad (7)$$

A tissue blood flow volume, a tissue blood volume and a mean transit time can be calculated based on the impulse response function $R_j$ calculated by above mentioned equation (7).

By the way, blood flows to capillaries in tissues. A time at which the contrast medium reaches a tissue depends on a place in the tissue, and therefore, the time axis of the artery TCC calculated with regard to a set arterial area is not same to that of the tissue TCC at each pixel strictly. Therefore, a contrast concentration in the tissue rises before that in the artery rises (the tissue TCC rises precedently before the artery TCC rises) in the extreme case.

In the above mentioned standard SVD method it is assumed that such a delay in the time direction does not occur. However, a deconvolution result changes depending on a delay time which is a difference in the time direction always existing between the artery TCC and tissue TCC. Consequently, the calculated tissue blood flow undergoes influence.

For that reason, the block circulant SVD method uses a system matrix which is a block circular matrix as shown in following equation (8) in order to reduce the dependence on the delay in the time direction.

$$\begin{pmatrix} C_{i_{bs}} \\ C_{i_{bs}+1} \\ \vdots \\ C_{i_{bs}+2L-1} \end{pmatrix} = \begin{pmatrix} b_{0,0} & b_{0,1} & \ldots & b_{0,i_{bs}+2L-1} \\ b_{1,0} & b_{1,1} & \ldots & b_{1,i_{bs}+2L-1} \\ \vdots & \vdots & & \vdots \\ b_{i_{bs}+2L-1,0} & b_{i_{bs}+2L-1,1} & \ldots & b_{i_{bs}+2L-1,i_{bs}+2L-1} \end{pmatrix} \begin{pmatrix} X_0 \\ X_1 \\ \vdots \\ X_{2L-1} \end{pmatrix} \quad (8)$$

When $i \geq j$ $b_{i,j} = \begin{cases} A_{i-j+i_{bs}} & \text{for } i-j < L \\ 0 & \text{otherwise} \end{cases}$ When $i < j$ $b_{i,j} = \begin{cases} A_{i-j+i_{bs}+L} & \text{for } i-j+L \geq 0 \\ 0 & \text{otherwise} \end{cases}$ The basic processing of the block circulant SVD method is similarly to that in the standard SVD method. That is, the matrix form of the block circulant SVD method is C=AX. However, A of the block circulant SVD method is a 2L×2L coefficient matrix. Accordingly, zeros are added rearward the respective element values constituting the tissue TCC in the column vector C to expand the coefficient matrix A, the column vector X and the column vector C to have double numerical elements of that in measured data. Especially, the coefficient matrix A is expanded to have double numerical rows and columns and above and rearranged so that elements in the column vector become periodic.

By composing a system matrix as shown in above mentioned equation (8), the impulse response function shifts in the time direction while keeping its shape a similar figure when a difference in the time direction exists. Therefore, shifting the impulse response function in the time direction makes it possible to calculate a tissue blood flow, a tissue blood volume and a mean transit time having reduced dependence on a delay in the time direction.

However, the size of the coefficient matrix A constituting the artery TCC becomes 2×2 times and the size of the column vector constituting the tissue TCC becomes double in the system matrix. Therefore, the time of analysis processing for the block circulant SVD method increases up to over 8 times and the block circulant SVD method is not practical.

For that reason, the non-patent document 2 puts the system matrix of the standard SVD method into practice without increasing the time of analysis processing. Specifically, the proposed method in the non-patent document 2 uses the system matrix shown by above mentioned equation (4) and excludes elements, which are within the head phase to an offset timing, in the tissue TCC from the known vector and calculation to compensate delay in this case, elements at some initial phases from the vector C to the offset timing are excluded from calculation by above mentioned equation (3) and instead of elements of which number is the same as that of the excluded elements are added to backward of the elements of the tissue TCC.

In this way, technique of the non-patent document 2 makes the dependence on the delay in the time direction small without extending the system matrix.

Because the technique of the non-patent document 1 does not consider the delay in the time direction with regard to the standard SVD method, the result of the deconvolution lacks sufficient accuracy. On the other hand, the block circulant SVD method requires much time for analysis processing though the delay in the time direction is considered. Therefore, it is a problem that both the standard SVD method and the block circulant SVD method are not practical.

Especially, X-ray CT apparatuses and MRI apparatuses are generally used for examinations of many patients. Further, analysis processing must be performed immediately after imaging and an operator must observe a result of the processing to determine whether the imaging has been performed appropriately or not. Therefore, if the time for analysis processing increases, the number of examinations which can be performed decreases, a waiting time of a patient increases and the number of patients processed by a certain hospital decreases. That is, increasing the time for analysis processing brings disadvantages to both patients and hospitals.

To such problem, the technique of the non-patent document 2 performs analysis processing without increasing processing time. However, a new problem occurs in that the processing result depends on an offset timing since elements, which are within the head phase to the offset timing, of the tissue TCC are excluded from calculation. Furthermore, it is difficult to identify the offset timing accurately. As a result, it is a problem that information on blood flow perfusion cannot be obtained stably.

[Non-patent document 1] Ona Wu et al, "Tracer Arrival Timing-insensitive. Technique for Estimating Flow in MR Perfusion-Weighted imaging Wine Singular Value Decomposition With a Block-Circulant Deconvolution Matrix", Magnetic. Resonance in Medicine 50: 164-174 (2003)

[Non-patent document 2] M. R. Smith, H. Lu, S. Trochet, and R. Frayne "Removing the Effect of SVD Algorithmic Artifacts Present in Quantitative MR Perfusion Studies", Magnetic Resonance in Medicine 51: 631-634 (2004)

DETAILED DESCRIPTION

Figure 1:
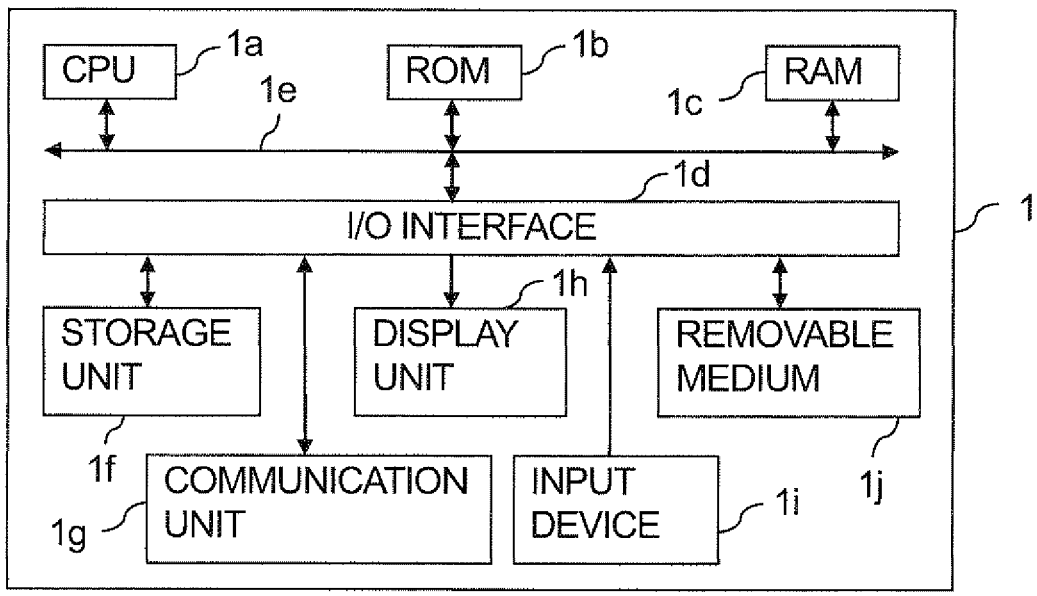
FIG. 1 is a diagram showing an example configuration of a blood flow perfusion analyzing apparatus according to a first embodiment of the present invention.

In general, according to one embodiment, a blood flow perfusion analyzing apparatus includes a tissue time concentration curve calculation unit, an arterial time concentration curve calculation unit a first making unit, a second making unit, a deconvolution unit and a blood flow information calculation unit. The tissue time concentration curve calculation unit is configured to measure a variation in pixel value between time phases at each pixel based on contrast image data of an object to obtain time concentration curves each showing a time variation in amount corresponding to a concentration of a contrast medium in a tissue. The contrast image data corresponds to the time phases. The contrast image data is acquired by a medical imaging apparatus. The arterial time concentration curve calculation unit is configured to set an arterial region based on the time concentration curves corresponding to the tissue and to calculate a time concentration curve corresponding to an artery. The first making unit is configured to make the time concentration curves corresponding to the tissue discrete with setting a first time as a first datum to make first sets. Each of the first sets has one-dimensionally arrayed elements including values corresponding to concentrations of the contrast medium at different times in the tissue. The second making unit is configured to make the time concentration curve corresponding to the artery discrete with setting a second time as a second datum to make a second set in which elements including values corresponding to concentrations of the contrast medium at different times in the artery are arrayed two-dimensionally. The second time is set to be after the first time. The deconvolution unit is configured to calculate transfer functions of the tissue by deconvolution with regard to each of the first sets and the second set. The blood flow information calculation unit is configured to calculate information on blood flow perfusion based on the transfer functions.

Further, according to another embodiment a blood flow perfusion analyzing method includes measuring a variation in pixel value between time phases at each pixel based on contract image data of an object to obtain time concentration curves each showing a time variation in amount corresponding to a concentration of a contrast medium in a tissue; setting an arterial region based on the time concentration curves corresponding to the tissue and calculating a time concentration curve corresponding to an artery; making the time concentration curves corresponding to the tissue discrete with setting a first time as a first datum to make first sets; making the time concentration curve corresponding to the artery discrete with setting a second time as a second datum to make a second set in which elements including values corresponding to concentrations of the contrast medium at different times in the artery are arrayed two-dimensionally; calculating transfer functions of the tissue by deconvolution with regard to each of the first sets and the second set; and calculating information on blood flow perfusion based on the transfer functions. The contrast image data corresponds to die time phases. The contrast image data is acquired by a medical imaging apparatus. Each of the first sets has one-dimensionally arrayed elements including values corresponding to concentrations of the contrast medium at different times in the tissue. The second time is set to be after the first time.

Further, according to another embodiment, a fluid analyzing apparatus includes a concentration-variation calculation unit and a fluid information calculation unit. The concentration-variation calculation unit calculates a first variation in first amount and a second variation in second amount between frames based on pieces of image data of an object. The first amount depends on a concentration of a pixel value at each pixel corresponding to a tissue. The second amount depends on a concentration of a pixel value corresponding to a fluid. The pieces of image data correspond to the frames. The fluid information calculation unit makes first elements based on the first variation and second elements based on the second variation to calculate information on a perfusion of the fluid with deconvolution processing based on the first elements and the second elements. The first elements have a same number as analyzing targets and an initial element corresponding to a first point on the first variation. The second elements have die same number as the analyzing targets and an initial element corresponding to a second point on the second variation. The second point is set be after the first point.

Further, according to another embodiment, a fluid analyzing method includes calculating a first variation in first amount and a second variation in second amount between frames based on pieces of image data of an object, the first amount depending on a concentration of a pixel value at each pixel corresponding to a tissue, the second amount depending on a concentration of a pixel value corresponding to a fluid, the pieces of image data corresponding to the frames; and making first elements based on the first variation and second elements based on the second variation to calculate information on a perfusion of the fluid with deconvolution processing based on the first elements and the second elements, the first elements having a same number as analyzing targets and an initial element corresponding to a first point on the first variation, the second elements having the same number as the analyzing targets and an initial element corresponding to a second point on the second variation, the second point being after the first point.

Hereinafter, embodiments of the present invention will be described in detail with referring to drawings.

First Embodiment

FIG. 1 is a diagram showing an example configuration of a blood flow perfusion analyzing apparatus 1 according to a first embodiment of the present invention.

A blood flow perfusion analyzing apparatus 1 includes a CPU (Central Processing Unit) 1$a$, a ROM (Read Only Memory) 1$b$, a RAM (Random Access Memory) 1$c$ and an I/O (input/output) interface 1$d$ mutually connected through a bus 1$e$. A storage unit 1$f$, a communication unit 1$g$, a display unit 1$h$, an input device 1$i$ and a removable medium 1$j$ are connected with the I/O interface 1$d$.

The CPU 1$a$ reads a boot program to boot up the blood flow perfusion analyzing apparatus 1 from the ROM 1$b$ to execute the read program based on an input signal from the input device 1$i$ and also reads various operating systems stored in the storage unit 1$f$. In addition, the CPU 1$a$ controls various targets based on input signals from the input device 1$i$, reads a program or data stored in the ROM 1$b$ or the storage unit 1$f$ to load the read program or data to the RAM 1$c$ and executes a series of processings for data calculation, data process or the like based on commands of programs read from the RAM 1$c$.

The storage unit 1$f$, which is constituted by a semiconductor memory, a magnetic disk or the like, stores programs and data executed by the CPU 1$a$. For example, the storage unit 1$f$ prepares an application to analyze information on regional blood flow perfusion as a program executed by the CPU 1$a$. Hereinafter, this application to analyze information on regional blood flow perfusion is called a regional blood flow analysis application.

The communication unit 1$g$, which is constituted by a LAN (Local Area Network) card, a modem or the like, allows the blood flow perfusion analyzing apparatus 1 to communicate with a communication medium such as a LAN or the internet. That is, the communication unit 1$g$ transmits data, received from a communication medium, to the CPU 1$a$ through the I/O interface 1$d$ and the bus 1$e$ and data, received from the CPU 1$a$ through the I/O interface 1$d$ and the bus 1$e$, to a communication medium.

The display unit 1$h$ is a liquid crystal display for example. The display unit 1$h$ displays processing result by the CPU 1$a$ and so on, based on signals received from the CPU 1$a$ through the bus 1$e$ and the I/O interface 1$d$.

The input device 1$i$ is composed by input devices such as a key board and a mouse by which an operator of the blood flow perfusion analyzing apparatus 1 inputs various instructions. The input device 1$i$ generates an input signal based on an operation by an operator and transmits the input signal to the CPU 1$a$ through the I/O interface 1$d$ and the bus 1$e$.

The removable medium 1$j$ is an optical disk, a flexible disc or the like. Data read from the removable medium 1$j$ by a disk drive, which is not shown, is transmitted to the CPU 1$a$ through the I/O interface 1$d$ and the bus 1$e$ and data received from the CPU 1$a$ through the I/O interface 1$d$ and the bus 1$e$ is written in the removable medium 1$j$ by the disk drive.

The blood flow perfusion analyzing apparatus 1 according to the first embodiment analyzes a blood flow perfusion based on image data acquired by dynamic imaging with a medical imaging apparatus (so called medical modality) such as an X-ray CT apparatus or a MRI apparatus. Therefore, the blood flow perfusion analyzing apparatus 1 has only to be in a circumstance possible to obtain the above mentioned image data. The blood flow perfusion analyzing apparatus 1 may be configured together with a medical imaging apparatus as a unit. Alternatively, the blood flow perfusion analyzing apparatus 1 may be configured separately from a medical imaging apparatus. When the blood flow perfusion analyzing apparatus 1 is configured separately from a medical imaging apparatus, acquired data is transmitted from a medical imaging apparatus, which is not shown, to the blood flow perfusion analyzing apparatus 1 through the removable medium 1$j$ or the communication unit 1$g$.

The blood flow perfusion analyzing apparatus 1 also can transfer a result of blood flow perfusion analysis to a PACS (Picture Archiving and Communication System) through the communication unit 1$g$ to be stored in the PACS. Herewith it becomes possible to search and browse a result of blood flow perfusion analysis corresponding to specific image data easily.

Medical imaging apparatuses include an ultrasonic diagnostic apparatus and a PET (Positron Emission Tomography) apparatus as well as an X-ray CT apparatus and an MRI apparatus.

Figure 2:
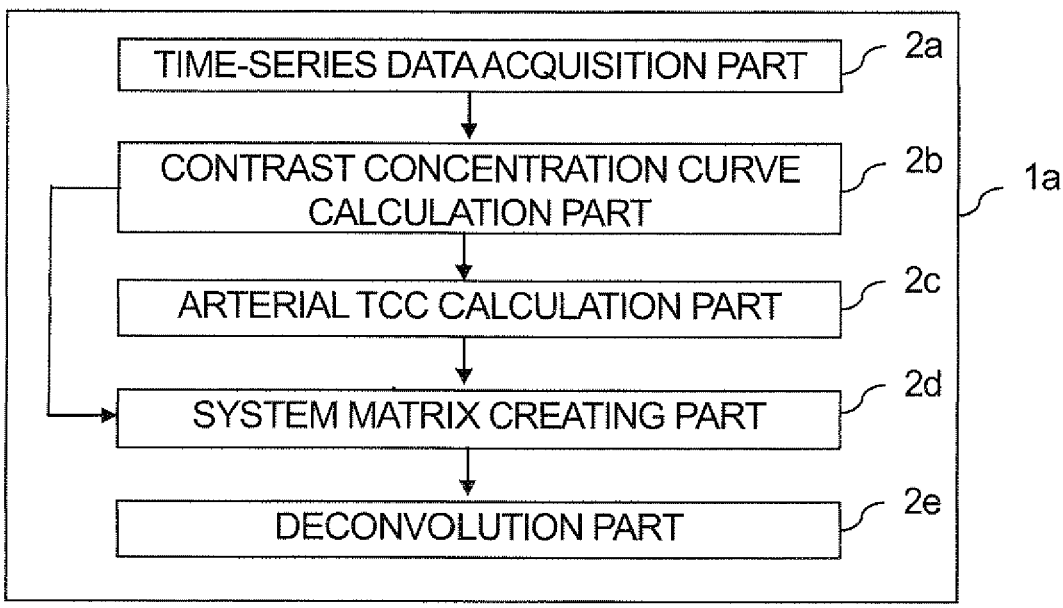
FIG. 2 is a block diagram showing an example of functions of the CPU executing the regional perfusion analysis application.

FIG. 2 is a block diagram showing an example of functions of the CPU 1$a$ executing the regional perfusion analysis application.

As shown in FIG. 2, the CPU 1$a$ executing the regional perfusion analysis application functions as a time-series data acquisition part 2$a$, a contrast concentration curve calculation part 2$b$, an arterial TCC calculation part 2$c$, a system matrix creating part 2$d$ and a deconvolution part 2$e$.

The time-series data acquisition part 2$a$ acquires time-series imaging data (pieces of image data at many time phases) generated by imaging of an object, in which contrast medium was injected (bolus-injected) in a vein, for a predetermined period with a medical imaging apparatus to send the acquired time-series imaging data to the contrast concentration curve calculation part 2$b$.

The contrast concentration curve calculation part 2$b$ inputs the time-series imaging data sent from the time-series data acquisition part 2$a$ and measures changes in pixel values at respective pixels to calculate contrast concentration curve s.

That is, contrast medium injected in a vein of an object in a relatively short time returns to the heart through veins, circulates the lung, returns to the heart again, flows into arteries, reaches tissues in respective organs and returns to the heart through the veins again. Therefore, when time-series CT images or MR images in a cerebral region are acquired with a medical imaging apparatus, changes in pixel values at respective pixels depending on changes in densities of the contrast medium can be measured for example. The contrast concentration curve calculation part 2$b$ can calculate contrast concentration curves based on the above mentioned measured changes in pixel values at the respective pixels.

For example, in case of CT images, each of TDCs (Time Density Curves), which are quantities proportional to densities of contrast medium, is calculated by subtracting a pixel value $S_0$ before the arrival of the contrast medium from a pixel value $S_i$ at each time phase as shown in following equation (9). As for equation (9), i represents a time phase in imaging.

$$C_i = S_i - S_0 \quad (9)$$

Alternatively, in case of MR images, each of TCCs (Time Concentration Curves), which are quantities ($\Delta R2^*$) proportional to densities of contrast medium, is calculated based on a logarithm of a ratio of a pixel value $S_i$ at each time phase to a pixel value $S_0$ before the arrival of the contrast medium as shown in following equation (10). As for equation (10), i represents a time phase in imaging and TE represents an echo time.

$$\Delta R2^* = -\log(S_i/S_0)/TE \quad (10)$$

The contrast concentration curve calculation part. $2b$ sends the contrast concentration curves calculated by above-mentioned equation (9) or equation (10) to the arterial TCC calculation part $2c$ and the system matrix creating part. $2d$ as tissue TCCs $C_i$.

The contrast concentration curve calculation part $2b$ functions as a tissue TCC calculation unit configured to measure a variation in pixel value between time phases at each pixel based on contrast image data of an object, which corresponds to the time phases, to obtain a time concentration curve showing a time variation in amount corresponding to a concentration of a contrast medium in a tissue.

The arterial TCC calculation part $2c$ inputs the tissue TCCs $C_i$ output from the contrast concentration curve calculation part $2b$ and calculates an arterial TCC at a voxel, which is an analysis unit for a CT image and a MRI image, based on the curve. Specifically, each voxel, which becomes an analysis unit for a CT image and a MRI image, has a size of about 0.5 mm to 3 mm, and therefore, some voxels are surely included in a blood vessel so long as the blood vessel is a main artery in a tissue.

The arterial TCC calculation part $2c$ functions a unit configured to specify such a voxel automatically or by instruction from a user to set an arterial region and calculate a TTC (the concentration value $a_i$ at the i-th imaging time in this case) for the arterial region. Note that, when plural voxels are specified as an arterial region, average values of the voxel values are set to $a_i$ for example.

Alternatively, the arterial TCC calculation part $2c$ applies a function specified as constant number times a gamma probability density function (i.e., a function proportional to the gamma probability density function) as shown by following equation (11) as a curve model of arterial TCC (hereinafter referred to as "arterial curve model") to perform curve fitting of the calculated arterial TCC $a_i$ (applying the calculated arterial TCC $a_i$ to the arterial curve model), as needed. Generally, curve fitting is often performed with regard to MRI images while curve fitting is not often performed with regard to CT images.

$$\phi(t; t_0, \alpha, \beta, K) = K(t - t_0)^\alpha \exp\{-\beta^{-1}(t - t_0)\} \quad (11)$$

The above-mentioned gamma probability density function expresses a probability density of a time required for passing through all of α barriers which can be passed through at a ratio of once per a time β. The arterial function can be considered as a function dispersed by passing through barriers of a lung. Accordingly, the gamma probability density function is applied as the arterial curve model for applying the calculated arterial TCC $a_i$ to the arterial curve model (approximation)

The arterial TCC a(t) is expressed as following equation (12) by curve fitting with the function of constant number times the gamma probability density function expressed by above-mentioned equation (11). As for equation (12), t represents time and each of $t_0$, α, β and K represents a parameter. Specifically, α represents the number of barriers, β represents a time required for passing through all of α barriers and K represents a linear parameter.

$$a(t) = \phi(t; t_0, \beta, \beta, K) \quad (12)$$

The arterial TCC calculation part $2c$ calculates the four parameters of $t_0$, α, β and K in above-mentioned equation (12) which minimize square errors, shown in following equation (13), among the arterial curve model and concentration values $a_i$ of the artery Actually, a specific time before the contrast medium reaches a target organ is set to $t_0$ and the remaining α, β and K are calculated in many cases.

$$\sum_i (a(i\Delta t) - a_i)^2 \quad (13)$$

The arterial TCC calculation part $2c$ outputs the values of the arterial TCC $a_i$ calculated by curve fitting to the system matrix creating part $2d$.

The system matrix creating part $2d$ inputs the values of the tissue TCC $C_i$ output from the contrast concentration curve calculation part $2b$ and the values of the arterial TCC $a_i$ output from the arterial TCC calculation part $2c$.

The system matrix creating part $2d$ determines a head phase $i_{bs}$ and a phase range $i_{bs} \leq i \leq i_{bs} + L - 1$ to be an analyzing target from the input the tissue TCC $C_i$ and the arterial TCC $a_i$. As the head phase $i_{bs}$ to be the analyzing target, a phase at or after which the concentrations of the contrast medium in the artery and the tissue begin to rise is used. A phase means a time defined by a sampling interval in an analysis and a phase range means a range to be analyzed.

The system matrix creating part $2d$ calculates pieces of data discrete in the time axis direction, which are L pieces of data obtained by dividing the determined phase range of $i_{bs} \leq i \leq i_{bs} + L - 1$ into L equal sections, by making the phase range of the arterial TCC $a_i$ discrete in the time axis direction as shown in following equation (14).

$$A_i = a(i T_R) \quad (14)$$

In above-mentioned equation (14). $T_R$ represents a time interval in imaging (repetition time).

The system matrix creating part $2d$ adds H elements to ahead of a set, which is obtained by making the tissue TCC $C_i$ discrete in the time axis direction and consists of concentration values corresponding to the tissue at different times, in the time axis direction.

Herewith, a (H+L)×1 column vector is made. Specifically, a first set, which consists of elements including concentration values corresponding to the tissue at the different times and the H elements added to ahead of the head phase $i_{bs}$, is arrayed one-dimensionally in the time axis direction into the column vector. In this case, a time for starting data acquisition or a predetermined time (N-th phase after the time for starting the data acquisition) becomes a datum for the initial phase corresponding to the initial element of the first set.

The system matrix creating part $2d$ function as a first making unit, configured to make a TCC corresponding to the tissue discrete with setting a first time (a time for starting data acquisition or N-th phase after the time for starting the data acquisition) as a first datum to make the first set in which the elements including values corresponding to concentrations of the contrast medium at different times in the tissue are arrayed one-dimensionally.

In addition, the system matrix creating part 2d adds H elements to afterward of a set, which is obtained by making the arterial TCC $A_i$ discrete in the time axis direction and consists of concentration values corresponding to the artery at different times, in the time axis direction. Herewith, a (L+H)×1 column vector is made. Specifically, the second set consisting of elements including the concentration values corresponding to the artery at the different times is arrayed one-dimensionally in the time axis direction into the column vector. Further, the system matrix creating part 2d makes a (L+H)×(L+H) coefficient matrix in which column vectors, each arrayed one-dimensional and consisting of the concentration values corresponding to the artery, are arrayed two-dimensionally in the spatial direction.

Herewith, the second set consisting of the elements including the concentration values corresponding to the artery at the different times is arrayed two-dimensionally in the time axis direction and the spatial direction to make the (L+H)×(L+H) coefficient matrix. In this case, the head phase $i_{bs}$ to be the analyzing target becomes a datum for the initial phase corresponding to the initial element of the second set.

The system matrix creating part 2d also functions as a second making unit configured to make the time concentration curve corresponding to the artery discrete with setting a second time (the time at which the time concentration curve corresponding to the artery begins to rise) after the first time (the time for starting the data acquisition or the N-th phase after the time for starting the data acquisition) as a second datum to make the second set in which the elements including the values corresponding to the concentrations of the contrast medium at the different times in the artery are arrayed two-dimensionally.

The system matrix creating part 2d creates a system matrix of C=AX, wherein C is the column vector consisting of the element including the concentration values at the different times in the tissue, A is the coefficient matrix consisting of the elements including the concentration values at the different times in the artery and X is a set of unknown quantities (an impulse response function) respectively made as described above, as shown in following equation (15) since the tissue TCC is derived by deconvolution of the arterial TCC and the impulse response function. In equation (15), C is the (H+L)×1 vector, A is the (L+H)×(L+H) matrix and X is a (L+H)×1 vector. The sign $i_{bs}$ represents the head phase to be the analyzing target.

$$\begin{pmatrix} P_0 \\ \vdots \\ P_{H-1} \\ C_{i_{bs}} \\ \vdots \\ C_{i_{bs}+L-1} \end{pmatrix} = \begin{pmatrix} a_{0,0} & a_{0,1} & \cdots & a_{0,L+H-1} \\ a_{1,0} & a_{1,1} & \cdots & a_{1,L+H-1} \\ \vdots & \vdots & & \vdots \\ a_{L+H-1,0} & a_{L+H-1,1} & \cdots & a_{L+H-1,L+H-1} \end{pmatrix} \begin{pmatrix} X_0 \\ X_1 \\ \vdots \\ X_{L+H-1} \end{pmatrix} \quad (15)$$

As for above-mentioned equation (15), H represents the number of the elements to be added to the L×L coefficient matrix. For example, H may be the number of sections obtained by dividing a range from the time for starting imaging (data acquisition) to the head phase by a phase interval and above or below Decreasing the number H of the added elements reduces the size of the matrix to be analyzed, which shortens a processing time. However, a too few number H of the added elements increases the dependency on a data shift in the time direction. Therefore, the number of the sections obtained by dividing the range from the time for starting imaging to the head phase by the phase interval is enough one to reduce die dependency on the data shift in the time direction.

The elements each having a value of zero are input (added) as the added elements $P_i$ (i=0, 1, ..., H−1) out of the elements obtained by dividing the tissue TCC in the time axis direction. However, all or partial added elements may be measured values of the tissue TCC $C_i$. In this case, pieces of image data must be acquired at not lower than L phases actually.

The elements $a_{i,j}$, which are obtained by dividing the arterial TCC in the time axis direction, are expressed by following equation (16). In equation (16), i=0, 1, ..., L−1 and j=0, 1, ..., L−1.

$$a_{i,j} = \begin{cases} 0 & \text{for } i-j < 0 \\ A_{i-j+i_{bs}} & \text{for } 0 \le i-j \le L-1 \\ q_{ij} & \text{for } i-j \ge L \end{cases} \quad (16)$$

As for above-mentioned equation (16), the element having a value of zero is input (added) to each added element $q_{i,j}$. However, all or partial added elements $q_{i,j}$ may be measured values of the arterial TCC as shown in following equation (17). In this case, pieces of image data must be acquired at not lower than L phases actually.

$$q_{i,j}=A_{i-j+1_{bs}} \quad (17)$$

The system matrix creating part 2d outputs above-mentioned created equation (15) to the deconvolution part 2e.

The deconvolution part 2e functions as a deconvolution integration unit configured to input the coefficient matrix output from the system matrix creating part 2d and perform deconvolution using the SVD method, the Fourier transformation method or the like. The deconvolution part 2e calculates the impulse response function $R_i$ based on the unknown quantities X calculated by the deconvolution as shown in above-mentioned equation (7).

The deconvolution part 2e searches a range in which a peak phase (a maximum value of the impulse response function $R_i$) lies based on the impulse response function $R_i$ calculated by above-mentioned equation (7) and calculates a peak range (width) based on the searched peak phase.

Figure 3:
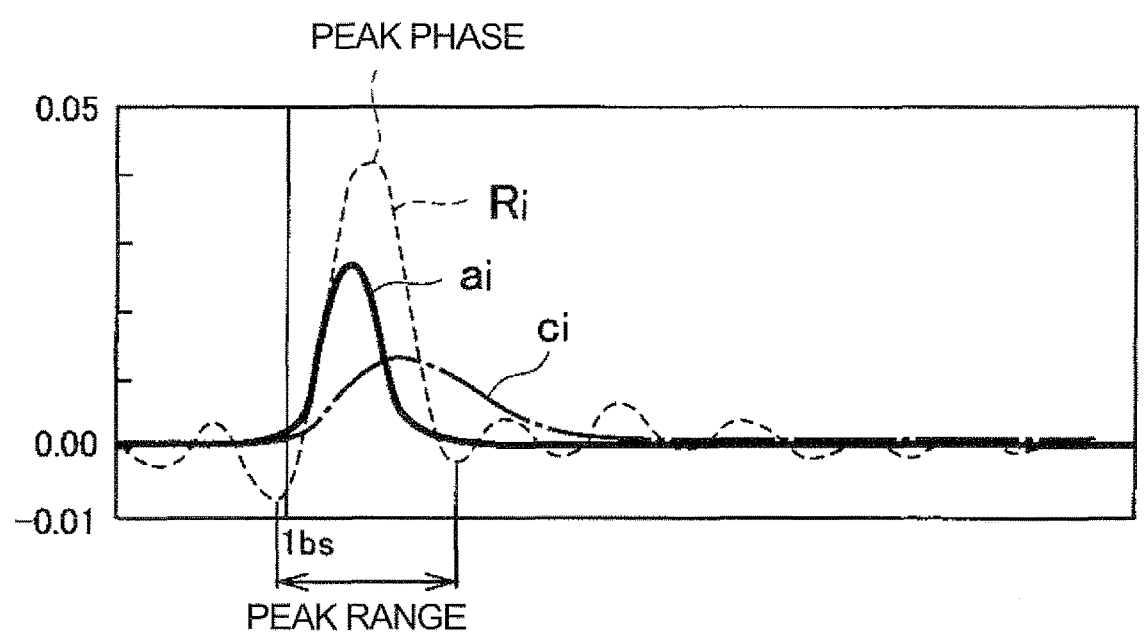
FIG. 3 is a graph for explaining a peak phase.

FIG. 3 is a graph for explaining a peak phase.

As shown in FIG. 3, the peak of the impulse response function $R_i$ calculated in the first embodiment lies in a phase later than that in the conventional standard SVD method by a time corresponding to the H elements. Therefore, the deconvolution part 2e must consider the shift of the peak phase in the late direction. Accordingly, the peak range must be determined previously to calculation of information on a regional blood flow perfusion.

Examples of method for calculating the peak range include a method for searching the peak phase from the head phase toward the time axis direction and setting a range between phases, at which the impulse response function $R_i$ shows negative local minimal values before and after the searched peak phase, as the peak range. Alternatively, a range between phases at which the impulse response function $R_i$ shows zero instead of the negative local minimal values may be set as the peak range.

The deconvolution part 2e calculates a MTT (Mean Transit Time), a CBF (Cerebral Blood Flow) and a CBV (Cerebral Blood Volume), which are information on the regional blood flow perfusion, based on the searched peak phase and peak range as shown in following equation (18). That is, the CBF can be calculated based on a height of the peak on the impulse response curve, the CBV can be calculated based on an area of the peak range of the impulse response curve and the MT can be calculated based on the peak range of the impulse response curve.

$$CBF = MAX(R_i)$$

$$CBV = SUM(R_i)$$

$$MTT = SUM(R_i)/MAX(R_i) \quad (18)$$

The deconvolution part 2e also functions as a blood flow information calculation unit configured to calculate information on blood flow perfusion based on the transfer function of the tissue (the impulse response function).

Further, the deconvolution part 2e corrects the calculated MTT, CBF and CBV as shown in following equation (19).

$$CBV = (100 \ h/\rho) T_R SUM(R_i)$$

$$CBF(r) = 60(100 \ h/\rho) MAX(R_i)$$

$$MTT2(r) = T_R \{SUM(R_i)/MAX(R_i)\} \quad (19)$$

As for above-mentioned equation (19), $\rho$ represents the specific gravity of the brain and h represents a hematocrit value (a rate of erythrocytes included in a constant quantity of blood). Alternatively, the CBF may be corrected (calculated) according to the relation of following equation (20).

$$CBF = CBV/MTT2 \quad (20)$$

Figure 4:
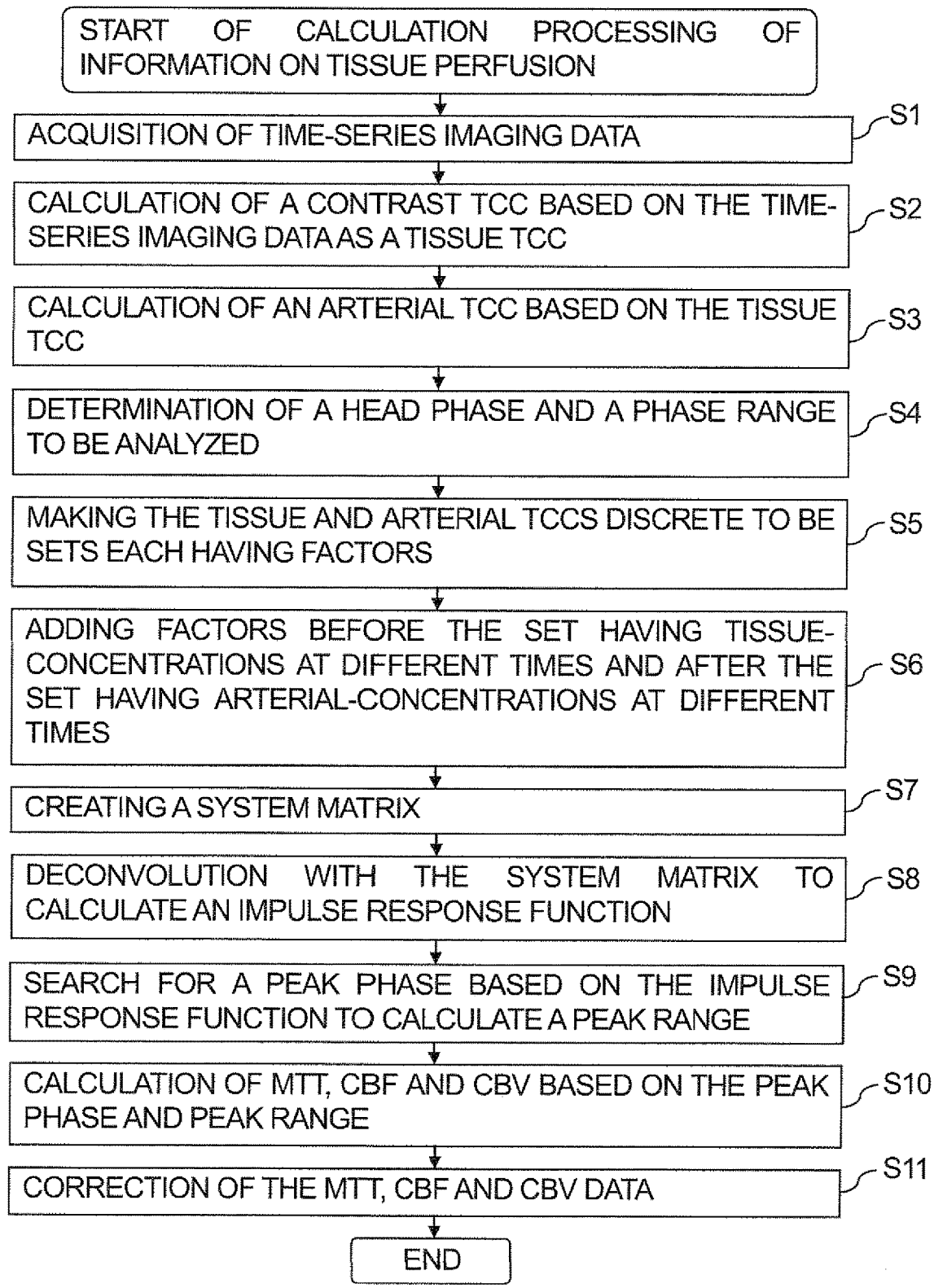
FIG. 4 is a flowchart which explains calculation processing of information on perfusion in a tissue.

Next, explanation will be made for processing of calculating information on a blood flow perfusion in a tissue in the first embodiment with referring to a flowchart of FIG. 4. Especially; processing for calculating information on blood flow perfusion in a cerebral tissue will be described for example.

In step S1, the time-series data acquisition part 2a acquires time-series pieces of imaging data generated by imaging during a specific period with a medical imaging apparatus.

In step S2, the contrast concentration curve calculation part 2b calculates contrast concentration curves based on the time-series pieces of the imaging data acquired in the processing of step S1 by measuring a variation in pixel value at each pixel. Each contrast concentration curve is set to a tissue TCC $C_i$.

In step S3, the arterial TCC calculation part 2c sets an arterial region, which becomes an analyzing target on CT images or MR images, based on the tissue TCCs $C_i$ calculated in the processing of step S2 and calculates a TCC $a_i$ for the set arterial region. At this time, the arterial TCC calculation part 2c applies a function of a constant times a gamma probability density function as an arterial curve model to perform curve fitting of the calculated arterial TCC $a_i$ when the acquired pieces of the imaging data are MR images.

In step S4, the system matrix creating part 2d determines a head phase $i_{bs}$ and a phase range $i_{bs} \leq i \leq H+L-1$ to be an analyzing target.

In step S5, the system matrix creating part 2d divides the phase range $i_{bs} \leq i \leq H+L-1$, which is determined in the processing of step S4, of each tissue TCC $C_i$ calculated in the processing of step S2 in the time axis direction to make a column vector by one-dimensionally arranging a set consisting of concentration values corresponding to the tissue at different times derived by the division.

Further, in step S5, the system matrix creating part 2d divides the phase range $i_{bs} \leq i \leq H+L-1$, which is determined in the processing of step S4, of the arterial TCC $a_i$ calculated in the processing of step S3 in the time axis direction to make a coefficient matrix by two-dimensionally arranging a set consisting of concentration values corresponding to the artery at different times derived by the division.

In step S6, the system matrix creating part 2d adds H elements to ahead of the column vector (the set), which consists of the concentration values corresponding to the tissue at the different times and was made in the processing of step S5, in the time axis direction. Herewith, the head phase $i_{bs}$ to be the analyzing target is shifted in the time axis direction by a time corresponding to the H elements, and the first set, which consists of the elements including the concentration values corresponding to the tissue at the different times and starting from a starting time of an data acquisition or a predetermined time serving as a datum for initial element, is arrayed one-dimensionally into the $(H+L) \times 1$ column vector.

Further, in step S6, the system matrix creating part 2d adds H elements to afterward of the coefficient matrix (set), which consists of the concentration values corresponding to the artery at the different times and was made in the processing of step S5, in the time axis direction. Herewith, the second set consisting of the elements including the concentration values corresponding to the artery at the different times and starting from a phase at which the arterial contrast concentration begins to rise or one before the phase serving as a datum for initial element, is arrayed two-dimensionally into the $(L+H) \times (L+H)$ coefficient matrix A.

In step S7, the system matrix creating part 2d creates a system matrix shown in above-mentioned equation (15) using the column vector C, the coefficient matrix A and the unknown quantities X (the impulse response function). The column vector C is a vector obtained in the processing of step S6 and consists of the elements including the concentration values corresponding to the tissue at the different times. The coefficient matrix A is also a matrix obtained in the processing of step S6 and consists of the elements including the concentration values corresponding to the artery at the different times.

Figure 5:
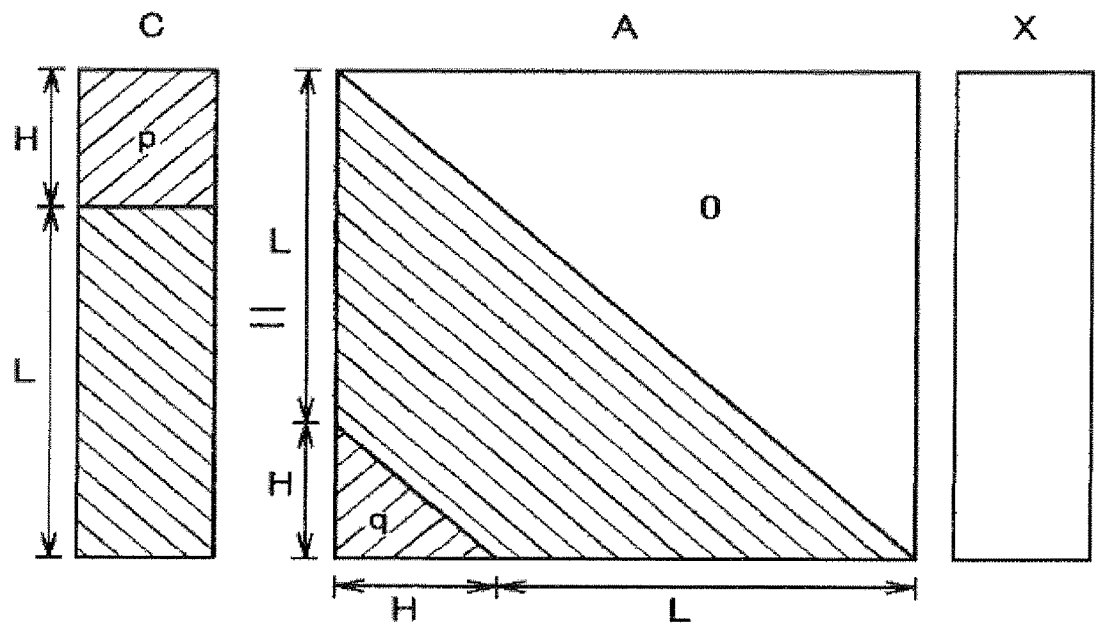
FIG. 5 is a schematic diagram showing a system matrix according to the first embodiment.

FIG. 5 is a schematic diagram showing a system matrix of the equation (15) according to the first embodiment.

In FIG. 5, C represents the $(H+L) \times 1$ column vector derived by dividing the tissue TCC $C_i$ in the time axis direction schematically, A represents the $(L+H) \times (L+H)$ coefficient matrix by dividing the arterial TCC $a_i$ in the time axis direction schematically and X represents the unknown quantities (the impulse response function) schematically.

As shown in FIG. 5, the H elements $p_i$ are added to ahead of the column vector constituting the tissue TCC while the H elements $q_{i,j}$ are added to afterward of the coefficient matrix A constituting the arterial TCC. The number H of the added elements is preferably to set to the number of the sections obtained by dividing the range from the time for starting the imaging to the head phase $i_{bs}$ by the phase interval. As each value of added elements $P_i$ (i=0, 1, ..., H−1) and qi,j, the element having the value of zero is input (added). However, actual measured values may be used as all or a part of the added elements.

Making the above mentioned system matrix makes it unnecessary to double a system matrix like the conventional block circulant SVD method, which leads to a high speed processing of deconvolution.

The explanation will be made with referring to FIG. 4 again, in step S8, the deconvolution part 2e performs deconvolution of the system matrix created by the processing of step S7 under the SVD method, the Fourier transform method or the like to calculates the vector X and the impulse response function $R_i$ based on the vector X as shown in above mentioned equation (7).

In step S9, the deconvolution part 2e searches a peak phase from the impulse response function $R_i$ calculated by the processing of step S8 and calculates a peak range based on the searched peak phase.

In step S10, the deconvolution part 2e calculates information on a regional blood flow perfusion including a MTT, a CBF and a CBV, based on the peak phase and the peak range calculated by the processing of step S9, according to above-mentioned equation (18).

In step S11, the deconvolution part 2e corrects the MTT, the CBF and the CBV, which are calculated by the processing of step S10 respectively, as shown in above-mentioned equation (19).

As described above, the blood flow perfusion analyzing apparatus 1 adds a predetermined number of elements to ahead of the column vector constituting the tissue TCC to be an analyzing target, adds a predetermined number of elements to afterward of the coefficient matrix constituting the arterial TCC aid shifts reference positions for the head phases of the tissue and arterial TCCs to be the same. Herewith, it becomes possible to reduce dependency on a shift in the time direction to stably calculate a MTT, a CBF and a CBV, which are information on blood flow perfusion in a blood vessel, without increasing a processing time.

Consequently, the hospital side becomes able to examine a lot of patients with shortening waiting times for examinations of patients. In addition, an analyzing result can be obtained stably. Therefore, the number of reexaminations (re-analyses) can be decreased, which reduces loads to patients.

Further, the blood flow perfusion analyzing apparatus 1 can display an image corresponding to the calculated MTT, CBV and CBF on the display unit 1h. Therefore, an operator can understand a state of a blood flow perfusion easily.

In the above description, a case where a cerebral tissue is target is explained for example. However, not only a cerebral tissue but also another tissue, such as a liver, a heart or a lung, may be a target in the first embodiment of course.

Further, in the above description, corrections with regard to a cerebral tissue are performed with a hematocrit value and the specific gravity of the brain. When a tissue, such as a liver or a lung, having a motion due to breaths or a heart is a target a correction of a tissue motion is important to be performed. In this case, not only a motion correction but also a correction with a hematocrit value and the other necessary corrections are important to be performed.

Second Embodiment

Figure 6:
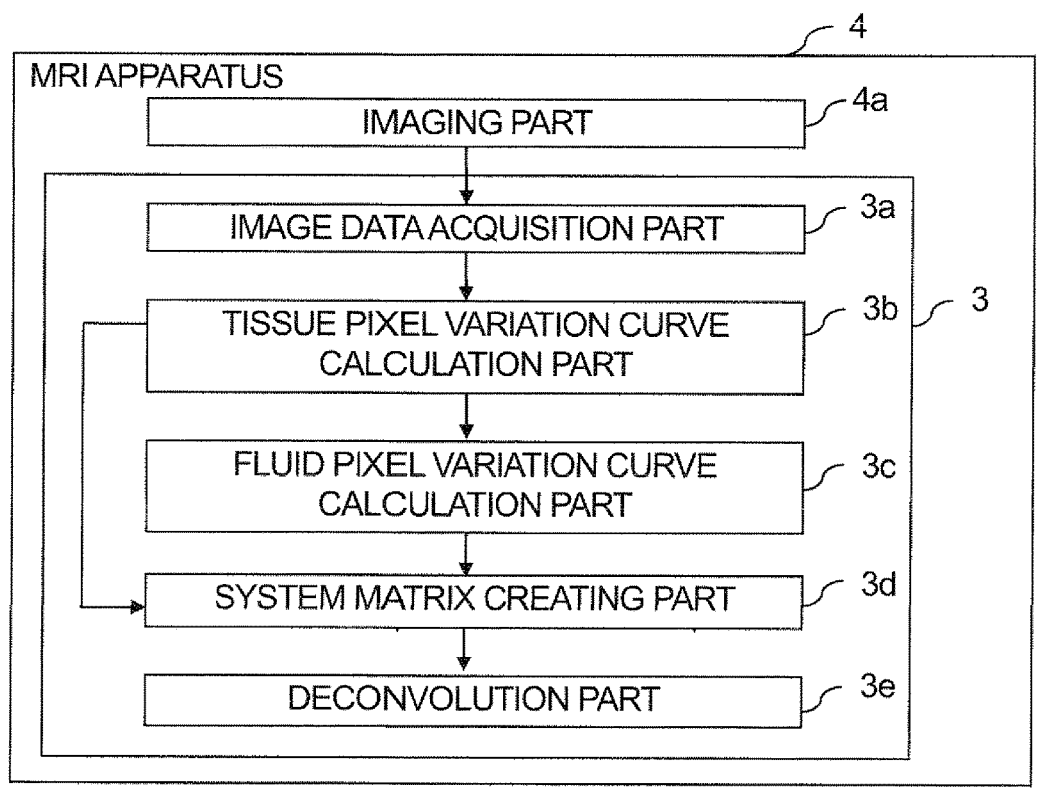
FIG. 6 is a functional block diagram which shows a configuration example of a fluid analyzing apparatus according to a second embodiment of the present invention.

FIG. 6 is a functional block diagram which shows a configuration example of a fluid analyzing apparatus according to a second embodiment of the present invention.

The fluid analyzing apparatus 3 is built in a MRI apparatus 4 for example. However, the fluid analyzing apparatus 3 may be connected with not only the MRI apparatus 4 but also an image processing apparatus or an image server which stores image data acquired by the MRI apparatus 4 through a network.

The MRI apparatus 4 includes an imaging part 4a. The imaging part 4 has a, function to perform non-contrast-enhanced imaging or contrast-enhanced imaging of fluid in an object to acquire pieces of non-contrast-enhanced fluid MR image data or contrast-enhanced fluid MR image data corresponding to multiple frames. Examples of fluid include blood flow in blood vessels and CSF (cerebrospinal fluid). Imaging of blood vessels by a MRI apparatus is referred to as MRA (magnetic resonance angiography).

More specifically the imaging part 4a includes elements such as a static field magnet, gradient coils, a gradient power supply, a transmission RF (radio frequency) coil, reception RF coils, a transmitter, a receiver, a sequencer, and a computer. The imaging part 4a applies gradient magnetic fields and RF pulses with the gradient coils and the transmission RE coil respectively to an object set in a static magnetic field inside the static field magnet, according to an imaging condition including a pulse sequence set by the computer. Then, NMR (nuclear magnetic resonance) signals generated in the object are received by the reception coils and image reconstruction processing of the NMR signals digitalized by the receiver is performed by the computer to generate MR image data. At this time, gradient magnetic pulses and RF pulses are applied to the gradient coils and the transmission RF coil from the gradient power supply and the transmitter respectively according to the pulse sequence output from the computer through the sequencer. Herewith, gradient magnetic pulses and RF pulses each having a desired waveform are applied to the object from the gradient coils and the transmission RF coil.

Figure 7:
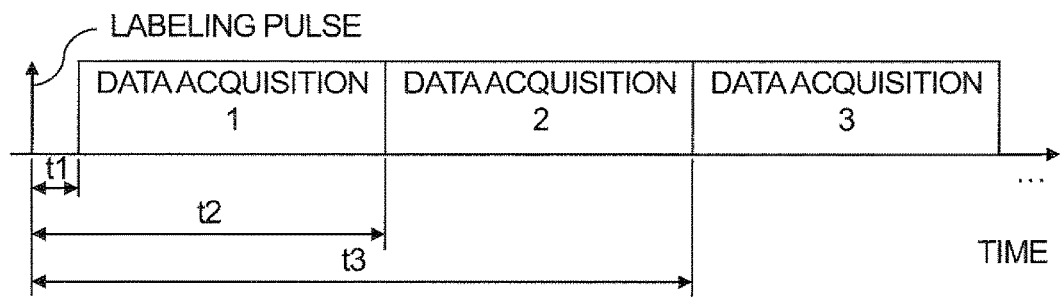
FIG. 7 is a chart which shows a first example of imaging condition or non-contrast-enhanced fluid imaging by the imaging pail in the MRI apparatus shown in FIG. 6.

FIG. 7 is a chart which shows a first example of imaging condition for non-contrast-enhanced fluid imaging by the imaging part 4a in the MRI apparatus 4 shown in FIG. 6.

In FIG. 7, the abscissa axis denotes time. FIG. 7 shows an example of pulse sequence for depicting an aperiodic CSF without contrast medium. As shown in FIG. 7, a labeling pulse (also referred to as a tagging pulse) is applied to the CSF or a target region, and subsequently, a dynamic scan which repeats an acquisition of imaging data (DATA ACQUISITION 1, DATA ACQUISITION 2, DATA ACQUISITION 3, . . . ) continuously over plural times are performed. Consequently, time-series pieces of non-contrast enhanced fluid image data corresponding to plural frames for mutually different times t1, t2, t3, . . . can be acquired.

As a labeling pulse, a t-SLIP (Time-SLIP: Time Spatial Labeling Inversion Pulse), a SAT (saturation) pulse (also referred to as a rest grid pulse), a SPAMM (spatial modulation of magnetization) pulse and a DANTE pulse are known. A same type of labeling pulse may be applied plural times. Alternatively, mutually different types of plural labeling pulses may be combined to be applied.

For example, combining plural region selective 90 degrees SAT pulses can form a region saturated into a radial or striped pattern in a selected slab region. Alternatively, applying a SPAMM pulse or a DANTE pulse also can form a region saturated into a desired pattern such as a striped pattern a grid pattern or a radial pattern. Therefore, pieces of dynamic CSF image data corresponding to plural frames showing a movement of the pattern together with a CSF flow can be acquired.

Imaging with a t-SLIP can be performed under a flow-in method and a flow-out method. Under the flow-in method, a region selective IR (inversion recovery) pulse out of the t-SLIP is applied to a target region and a CSF which is not labeled and flows into the target region from outside the target region are depicted. On the other hand, under the flow-out method, a region non-selective IR pulse and a region selective IR pulse out of the t-SLIP are applied and a labeled CSF flowing into a target region from a labeled region, to which the region selective IR pulse has applied, is depicted.

A labeling pulse may be applied in synchronization with a signal from a living body such as an ECG (electro cardiogram) signal, a synchronization signal from a breath sensor or a PPG (peripheral pulse gating) signal.

On the other hand, as a sequence for acquiring imaging data, an arbitrary sequence such as a SSFP (steady state free precession) sequence or a FASE (FastASE: fast asymmetric spin echo or fast advanced spin echo) can be used.

Figure 8:
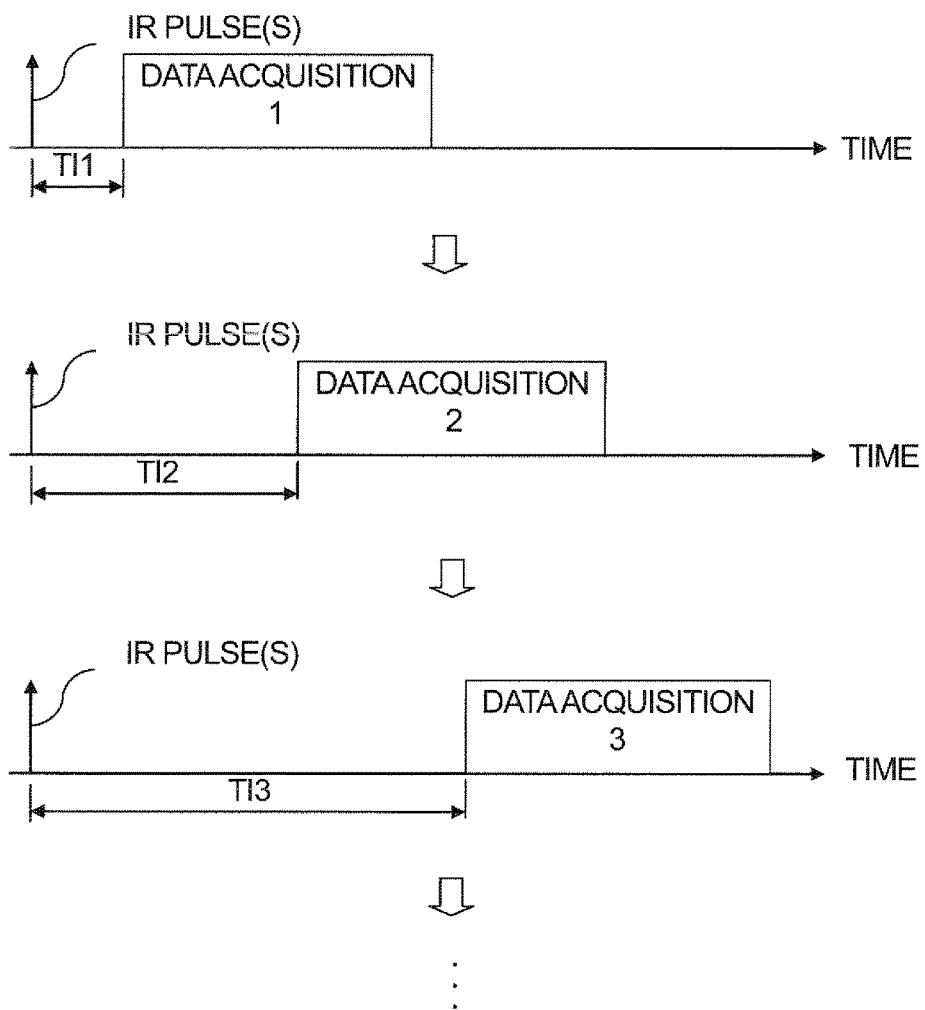
FIG. 8 is a chart which shows a second example of imaging condition for non-contrast-enhanced fluid imaging by the imaging part in the MRI apparatus shown in FIG. 6.

FIG. 8 is a chart which shows a second example of imaging condition for non-contrast-enhanced fluid imaging by the imaging part 4a in the MRI apparatus 4 shown in FIG. 6.

In FIG. 8, the abscissa axis denotes time and the ordinate direction also denotes time. FIG. 8 shows an example of pulse sequence for imaging fluid such as blood flow or CSF in an object using an IR pulse without contrast medium. Specifically, application of an IR pulse and acquisition of imaging data (DATA ACQUISITION 1, DATA ACQUISITION 2, DATA ACQUISITION 3, . . . ) are repeatedly performed with changing TI (inversion time) from the time for applying the IR pulse to a timing for acquiring the imaging data into TI1, TI2. TI3, . . . gradually.

A same type or different types of plural IR pulses as well as a single IR pulse may be applied at a sufficiently short interval which can be assumed to be simultaneous. A region selective IR pulse is applied to an imaging region in case of the above mentioned flow-in method while it is applied to a region upstream of an imaging region in case of the flow-out method. Thus, an imaging region or a fluid is labeled by tipping a magnetization in a desired target with a combination of a region selective IR pulse, a frequency selective IR pulse, a region non-selective IR pulse and a frequency non-selective IR pulse. Further image reconstruction processing of imaging data acquired from an imaging region at a timing at which the fluid travels by a distance depending on each TI generates fluid image data in which the fluid flowing into the imaging region is selectively depicted.

Herewith, it is possible to acquire pieces of non-contrast-enhanced fluid image data for frames corresponding to the mutually different TIs. That is, sorting the pieces of image data for the frames corresponding to the TIs in the order in which the TI increases can generate continuous pieces of image data showing an aspect that the fluid flows gradually according to the increase of the TI, just like dynamic image data.

Note that, application of an IR pulse and acquisition of imaging data may be synchronized with a signal from a living body such as an ECG signal to make velocities of the fluid at timings of data acquisition more constant. Imaging synchronized with a biosignal is preferable for imaging a periodic fluid such as blood flow.

Examples of a pulse sequence for acquiring imaging data include a SE (spin echo) sequence, a FSE (fast spin echo) sequence, a FASE sequence and an EPI (echo planar imaging) sequence.

Figure 9:
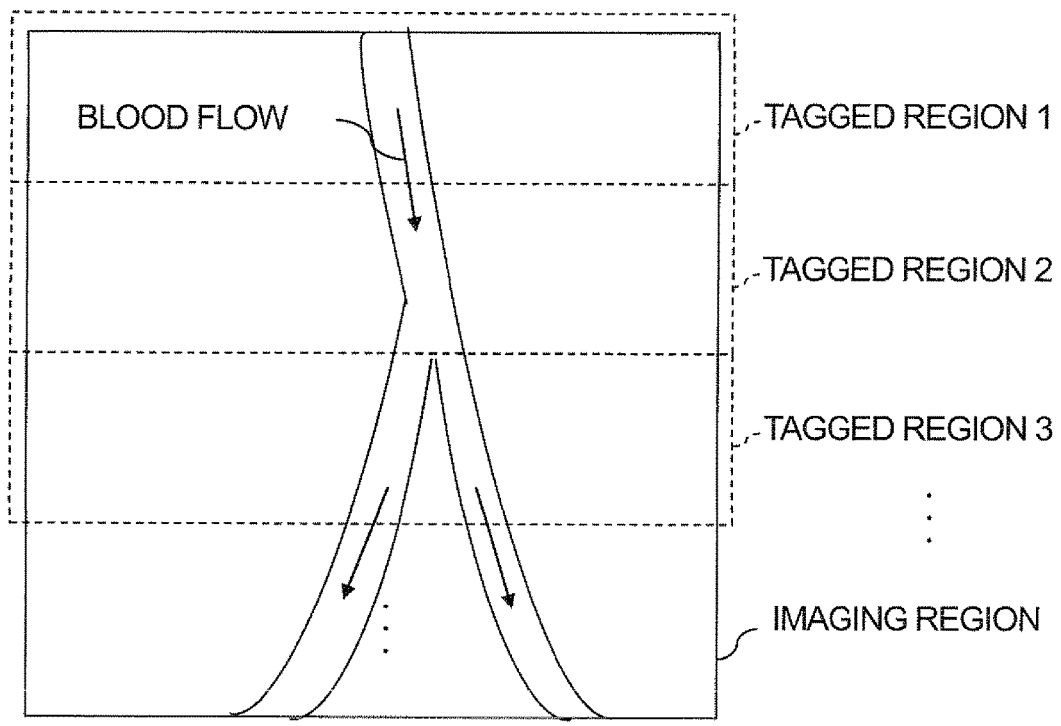
FIG. 9 is a chart which shows a third example of imaging condition for non-contrast-enhanced fluid imaging by the imaging part in the MRI apparatus shown in FIG. 6.

FIG. 9 is a chart which shows a third example of imaging conditions for non-contrast-enhanced fluid imaging by the imaging part 4a in the MRI apparatus 4 shown in FIG. 6.

Imaging by repeated application of a region selective IR pulse and acquisition of imaging data from an imaging region, which includes blood flows, as shown by solid lines in FIG. 9 while keeping a TI constant and changing a region, to which the region selective IR pulse is applied, into TAGGED REGION 1, TAGGED REGION 2, TAGGED REGION 3 . . . gradually as shown by dotted lines also can generate continuous pieces of image data depicting an aspect that the fluid flows gradually just like dynamic image data.

That is, blood flow in a region to which a region selective IR pulse is applied is labeled, and then, the labeled blood flow travels downstream by a distance corresponding to a TI out of the application region of the region selective IR pulse. At this timing, imaging data is acquired. Therefore, image data in which the labeled blood flow is selectively depicted can be generated.

Consequently, acquiring imaging data repeatedly with changes in the application region of a region selective IR pulse makes it possible to acquire pieces of non-contrast-enhanced fluid image data corresponding to plural frames to which mutually different plural labeled regions correspond respectively and in which labeled blood flows lie at different positions in the imaging region respectively.

Further, combining each of the pieces of the image data corresponding to the respective labeled regions with the pieces of the image data depicting blood flows at more upstream positions by composition processing such as MIP (maximum intensity projection) processing makes it possible to generate continuous pieces of image data showing an aspect that the blood flow travels gradually.

Note that, a SAT pulse may be used instead of an IR pulse in FIGS. 8 and 9.

Thus far, examples of imaging condition for non-contrast-enhanced imaging have been described. However contrast-enhanced image data may be acquired under a known contrast-enhanced imaging method similarly to the first embodiment. In this case, time-series pieces of contrast-enhanced image data are acquired for frames corresponding to plural time phases.

On the other hand, the fluid analyzing apparatus 3 has the function to acquire information expressing a fluid perfusion based on pieces of non-contrast-enhanced or contrast-enhanced fluid MR image data acquired by the imaging part 4a. For example, the fluid analyzing apparatus 3 can be made by installing a fluid analyzing program with an operation unit of a computer to make the computer function as an image data acquisition part 3a, a tissue pixel-variation curve calculation part 3b, a fluid pixel-variation curve calculation part 3c, a system matrix creating part 3d and a deconvolution part 3e. Alternatively a part of or all the fluid analyzing apparatus 3 may be made using circuits.

The image data acquisition part 3a has a function to acquire continuous pieces of fluid image data for plural frames acquired by the imaging part 4a and send the acquired pieces of the fluid image data to the tissue pixel-variation curve calculation part 3b.

The tissue pixel-variation curve calculation part 3b has a function to calculate variations in amount depending on concentration of fluid, such as labeled blood flow passing through a tissue, as tissue pixel-concentration variation curves respectively, based on variations in pixel value between the frames at pixels corresponding to a tissue out of the continuous pieces of the fluid image data for the frames and a function to output the calculated tissue pixel-concentration variation curves to the fluid pixel-variation curve calculation part 3c and the system matrix creating part 3d.

Note that, in case of non-contrast enhanced imaging method, contrast medium is not injected in fact. Therefore, in case of non-contrast enhanced imaging method, a logical concentration corresponding to a ratio of labeled fluid component to entire fluid quantity is calculated instead of a density in quantity of fluid component such as blood flow.

For example, a pixel value corresponding to the i-th value of a parameter such as time (t1, t2, t3, . . . ), a TI (TI1, TI2, TI3, . . . ) or a labeled region (TAGGED REGION 1, TAGGED REGION 2, TAGGED REGION 3, . . . ), changed between the frames is denoted by $S_i$ while a pixel value corresponding to a reference value, such as an initial value (t1, TI1, TAGGED REGION 1) of the parameter is denoted by $S_0$. Then, a variation in amount proportional to a pixel concentration in the tissue can be calculated as a pixel-concentration variation curve by equation (10) shown in the first embodiment. Alternatively, a TIC (time intensity curve) representing a variation in pixel value S self in the tissue corresponding to a parameter changed between the frames may be used as a pixel-concentration variation curve.

Each of the amount proportional to the pixel concentration and the pixel value becomes a quantity depending on a flow of the fluid. Therefore, the tissue pixel-concentration variation curve includes information on a fluid perfusion in the tissue.

The fluid pixel-variation curve calculation part 3c has a function to calculate a fluid pixel-concentration variation curve of fluid circulating in a fluid region such as an artery based on the tissue pixel-concentration variation curves at the pixels in the tissue and a function to output the calculated fluid pixel-concentration variation curve to the system matrix creating part 3d. The fluid pixel-concentration variation curve is a curve representing a variation in amount, depending on a pixel concentration corresponding to the fluid circulating in the fluid region, between the frames.

The fluid pixel-concentration variation curve can be calculated under a method similarly to that in the first embodiment. Therefore, the tissue pixel-concentration variation curves are calculated for the plural pixels respectively while the fluid pixel-concentration variation curve is calculated as a single curve consisting of a representing value of the amounts depending on the pixel concentrations of the fluid, similarly to the first embodiment. Accordingly, when a ROI (region of interest) including multiple pixels is set as a fluid part, a representing value of the amounts depending on the pixel values is calculated similarly to the first embodiment. The representing value may be calculated as an average value between the pixels for example. Alternatively, the representing value may be calculated by curve fitting with a function which is constant value times of gamma probability density function having fitting parameters as shown in equation (11). The pixels corresponding to the fluid region also can be specified automatically or by an instruction from a user similarly to the first embodiment.

The system matrix creating part 3d has a function to make a one-dimensional column vector C having elements consisting of the amounts depending on the pixel concentrations in the tissue at the respective values of the parameter such as time (t1, t2, t3, . . . ), the TI (TI1, TI2, TI3, . . . ) or the labeled region (TAGGED REGION 1, TAGGED REGION 2, TAGGED REGION 3, . . . ), based on the pixel-concentration variation curve corresponding to each of the pixels in the tissue and a function to make a one-dimensional column vector having elements consisting of the amounts depending on the pixel concentrations in the fluid at the respective parameter values based on the fluid pixel-concentration variation curve. In addition, the system matrix creating part 3d has a function to create a system matrix of C=AX using the column vector C, a coefficient matrix A and unknown quantities X and a function to output the created system matrix to the deconvolution part 3e. Here, the column vector C corresponds to the tissue and the coefficient matrix A is made by two-dimensionally arranging the column vectors corresponding to the fluid.

The column vector C corresponding to the tissue, the column vector corresponding to the fluid, the coefficient matrix A and the system matrix C=AX can be made by methods similarly to those in the first embodiment respectively. In other words, a following explanation is made.

Figure 10:
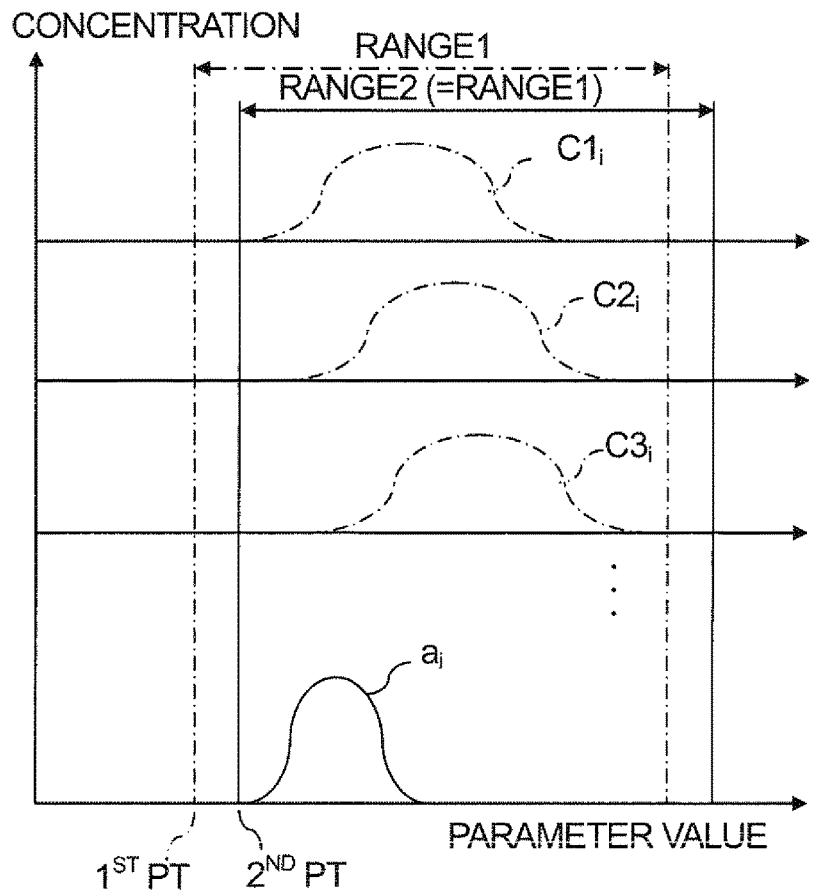
FIG. 10 is a diagram which explains a method of making elements to be analysis targets by the system matrix creating part shown in FIG. 6.

FIG. 10 is a diagram which explains a method of making elements to be analysis targets by the system matrix creating part 3d shown in FIG. 6.

In FIG. 10, the abscissa axis denotes parameter value, such as time (t1, t2, t3, . . . ), TI (TI1, TI2, TI3, . . . ) or labeled region (TAGGED REGION 1, TAGGED REGION 2, TAGGED REGION 3, . . . ) and the ordinate axis denotes pixel concentration.

As shown in FIG. 10, a case where pixel-concentration variation curves $C1_i$, $C2_i$, $C3_i$, . . . at respective pixels in a tissue and a fluid pixel-concentration variation curve $a_i$ are obtained is referred to in this case, a first point is determined at least before the respective tissue pixel-concentration variation curves $C1_i$, $C2_i$, $C3_i$, . . . rise while a second point is determined at least before the fluid pixel-concentration variation curve $a_i$ rises. For example, the first point is determined to an initial value (t1, TI1, TAGGED REGION 1) of the parameter, such as time (t1, t2, t3, . . . ), TI (TI1, TI2, TI3, . . . ) or labeled region (TAGGED REGION 1, TAGGED REGION 2, TAGGED REGION 3 . . . ), changed in imaging. On the other hand, the second point is determined to be a value which occurs in order after the first point.

In addition, a same width of ranges RANGE1 and RANGE2, which start from the first and second points respectively, are set on the tissue pixel-concentration variation curves $C1_i$, $C2_i$, $C3_i$, . . . and the fluid pixel-concentration variation curve $a_i$ respectively as analyzing targets so that the number of elements to be analyzing targets corresponding to each of the tissue pixel-concentration variation curves $C1_i$, $C2_i$, $C3_i$, . . . becomes same as that corresponding to the fluid pixel-concentration variation curve $a_i$. Incidentally, a part or all of the prior-occurring elements at parameter values within only the range RANGE1 to be the analyzing target on the tissue pixel-concentration variation curves $C1_i$, $C2_i$, $C3_i$, . . . may be set to zero value. On the other hand, a part or all of the subsequent elements at parameter values within only the range RANGE2 to be the analyzing target on the fluid pixel-concentration variation curve $a_i$ may be set to zero value.

As a result, an amount depending on each pixel concentration of the tissue at the first point or zero becomes the initial element to be an analyzing target corresponding to each of the tissue pixel-concentration variation curves $C1_i$, $C2_i$, $C3_i$, . . . while an amount depending on a pixel concentration of the fluid at the second point becomes the initial element to be an analyzing target corresponding to the fluid pixel-concentration variation curve $a_i$.

By using the same number of the elements corresponding to each of the tissue pixel-concentration variation curves and the elements corresponding to the fluid pixel-concentration variation curve made in this way, the system matrix as shown in equation (15) can be created.

The deconvolution part 3e has functions similarly to those of the deconvolution part 2e in the first embodiment. That is, the deconvolution part 3e has a function to calculate the unknown quantities X by deconvolution integration of the column vector C corresponding to the tissue and the coefficient matrix A in which the column vectors corresponding to the fluid are arrayed two-dimensionally and a function to calculate information on a fluid perfusion, such as a MTT of fluid a CBF, a CBV, a regional CSF flow and a regional CSF volume, based on an impulse response function derived from the unknown quantities X.

In addition, the deconvolution part 3e is configured to correct the information on the fluid perfusion as shown in equation (19), as needed, similarly to the deconvolution part 2e in the first embodiment.

Next, operation and action of the fluid analyzing apparatus 3 will be described.

Figure 11:
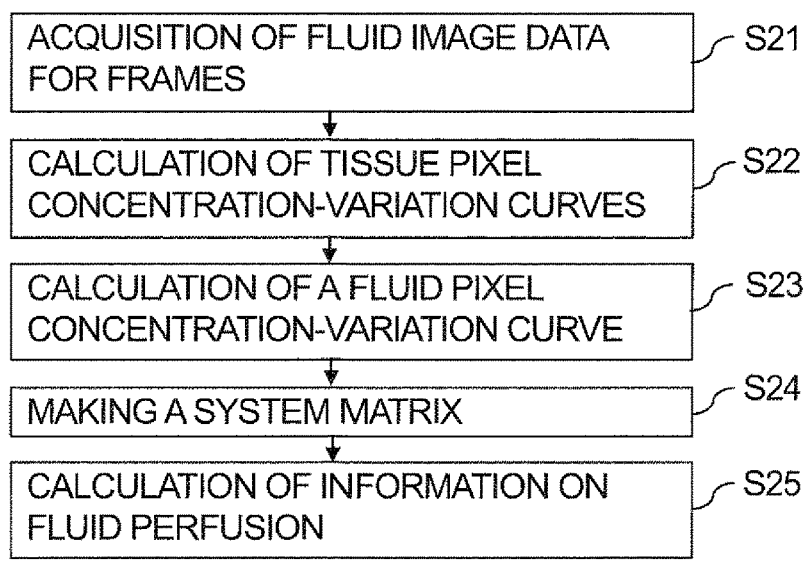
FIG. 11 is a flowchart which shows a flow for data processing in the fluid analyzing apparatus shown in FIG. 6.

FIG. 11 is a flowchart which shows a flow for data processing in the fluid analyzing apparatus 3 shown in FIG. 6. Note that, processing similarly to detail processing shown in FIG. 4 in the first embodiment is omitted.

Previously, the imaging part 4a of the MRI apparatus 4 performs non-contrast-enhanced imaging or contrast-enhanced imaging to acquire pieces of MR fluid image data for multiple frames.

Then, in step S21, the image data acquisition part 3a in the fluid analyzing apparatus 3 acquires the pieces of fluid image data for the multiple frames from the imaging part 4a and gives the acquired image data to the tissue pixel-variation curve calculation part 3b.

Next, in step S22, the tissue pixel-variation curve calculation part 3b calculates a variation in an amount depending on a concentration of a pixel value between frames at each of the respective pixels each corresponding to a tissue of the fluid image data for the multiple frames to obtain pixel-concentration variation curves of the tissue.

Next, in step S23, the fluid pixel-variation curve calculation part 3c calculate a pixel-concentration variation curve of the fluid based on the pixel-concentration variation curves at the respective pixels corresponding to the tissue.

Next, in step S24, the system matrix creating part 3d creates a system matrix of C=AX, wherein C represents a column vector corresponding to tissue pixel concentrations, A represents a coefficient matrix in which column vectors corresponding to fluid pixel concentrations are arranged two-dimensionally and X represents unknown quantities, based on the each tissue pixel-concentration variation curve and the fluid pixel-concentration variation curve. Here, a value, which corresponds to the first parameter value on the abscissa, axis, of each tissue pixel-concentration variation curve is set to the initial element of the column vector C corresponding to the tissue. On the other hand, a value, which corresponds to the second parameter after the first parameter value on the abscissa axis, of the fluid pixel-concentration variation curve is set to the initial element of the column vector corresponding to the fluid. Further, the respective column vectors are made so that the number of the elements in the column vector C corresponding to the tissue becomes as same as that corresponding to the fluid. For that reason, zero instead of pixel concentrations may be set as some elements constituting the respective column vectors.

Next, in step S25, the deconvolution part 3e calculates the unknown quantities X of the system matrix and subsequently calculates information on fluid perfusion based on an impulse response function obtained from the unknown quantities X. The information on the fluid perfusion may be corrected by equation (19).

In this way the fluid analyzing apparatus 3 can obtain information on perfusion of fluid such as blood flow or CSF, based on continuous pieces of non-contrast-enhanced image data corresponding to multiple frames acquired with changing an imaging parameter as well as time-series pieces of contrast-enhanced image data corresponding to multiple time phases, by processing similarly to that for contrast-enhanced image data.

Note that an explanation has been made for an example case where the fluid analyzing apparatus 3 calculates information on fluid perfusion based on pieces of image data acquired by a MRI apparatus in the second embodiment. However, the fluid analyzing apparatus 3 may be configured to calculate information on fluid perfusion based on pieces of non-contrast-enhanced image data or contrast-enhanced image data acquired by a medical imaging apparatus such as an X-ray CT apparatus, an ultrasonic diagnostic apparatus or a PET apparatus.

Other Embodiments

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A blood flow perfusion analyzing apparatus comprising:
at least one computer having a central processing unit (CPU) coupled to memory, display and input/output ports, said computer being configured by stored executable program instructions to
measure a variation in pixel value between time phases at each pixel based on contrast image data of an object to obtain time concentration curves each showing a time variation in amount corresponding to a concentration of a contrast medium in a tissue, the contrast image data corresponding to the time phases and being acquired by a medical imaging apparatus;
a define an arterial region based on the time concentration curves corresponding to the tissue and to calculate a time concentration curve corresponding to an artery;
make the time concentration curves corresponding to the tissue discrete by setting a first time as a first starting point time of sampling points for a first discretization of time concentration curves corresponding to the tissue to make first data sets, each of the first data sets having one-dimensionally arrayed elements including values corresponding to concentrations of the contrast medium at different times in the tissue;
make the time concentration curve corresponding to the artery discrete by setting a second time as a second starting point time of sampling points for a second discretization of a time concentration curve corresponding to the artery to make a second data set in which elements including values corresponding to concentrations of the contrast medium at different times in the artery are arrayed two-dimensionally, the second starting point time being after the first starting point time;
calculate transfer functions of the tissue by deconvolution with regard to each of the first data sets and the second data set;
calculate information on blood flow perfusion based on the transfer functions wherein the information on blood flow perfusion includes at least one of blood flow, mean transit time, or blood volume; and display the information on blood flow perfusion as a diagnostic aid.

2. The blood flow perfusion analyzing apparatus of claim 1,
wherein the first time is a time for starting an acquisition of the contrast image data or a predetermined time between the time for starting the acquisition and the second time while the second time is a time at which the time concentration curve corresponding to the artery begins to rise.

3. The blood flow perfusion analyzing apparatus of claim 1,
wherein each of the first data set is a set made by adding a number H of first elements to be disposed ahead of a set of one-dimensionally arrayed values in a time direction while the second data set is a set made by adding a second H number of elements to be disposed after a set of two-dimensionally arrayed values in the time direction, the one-dimensionally arrayed values corresponding to a number L concentrations of the contrast medium at the different times in the tissue, the two-dimensionally arrayed values corresponding to the number L concentrations of the contrast medium at the different times in the artery.

4. The blood flow perfusion analyzing apparatus of claim 3,
wherein each of the first H elements has a value of at least one of (a) zero and (b) a value corresponding to the concentration of the contrast medium in the tissue while each of the H second elements has a value of at least one of (a) zero and (b) a value corresponding to a concentration of the contrast medium in the artery.

5. The blood flow perfusion analyzing apparatus of claim 1,
wherein said computer is configured to search respective maximum values of the transfer functions and calculate peak ranges based on searched maximum values of the transfer functions to calculate the information on the blood flow perfusion based on the maximum values of the transfer functions and the peak ranges.

6. A blood flow perfusion analyzing method comprising:
using at least one computer configured to
measure a variation in pixel value between time phases at each pixel based on contrast image data of an object to obtain time concentration curves each showing a time variation in amount corresponding to a concentration of a contrast medium in a tissue, the contrast image data corresponding to the time phases and having been acquired by a medical imaging apparatus;
define an arterial region based on the time concentration curves corresponding to the tissue and calculating a time concentration curve corresponding to an artery;
make the time concentration curves corresponding to the tissue discrete by setting a first time as a first starting point time of sampling points for a first discretization of time concentration curves corresponding to the tissue to make first data sets, each of the first data sets having one-dimensionally arrayed elements including values corresponding to concentrations of the contrast medium at different times in the tissue;
make the time concentration curve corresponding to the artery discrete by setting a second time as a second starting point time of sampling points for a second discretization of a time concentration curve corresponding to the artery to make a second data set in which elements including values corresponding to concentrations of the contrast medium at different times in the artery are arrayed two-dimensionally, the second starting point time being after the first starting point time;
calculate transfer functions of the tissue by deconvolution with regard to each of the first data sets and the second data set;
calculate information on blood flow perfusion based on the transfer functions wherein the information on blood flow perfusion includes at least one of blood flow, mean transit time, or blood volume; and
display the information on blood flow perfusion as a diagnostic aid.

7. A blood or cerebral spinal fluid analyzing apparatus comprising:
at least one computer having a central processing unit (CPU) coupled to memory, display and input/output ports, said computer being configured by stored executable program instructions to
calculate a first variation as a first amount and a second variation as a second amount between image frames based on pieces of image data of an object, the first amount depending on a concentration of a pixel value at each pixel corresponding to a tissue, the second amount depending on a concentration of a pixel value corresponding to a blood or cerebral spinal fluid, the pieces of image data corresponding to image data derived from the frames;
make first elements based on the first variation and second elements based on the second variation and to calculate information on a perfusion of the blood or cerebral spinal fluid with deconvolution processing based on the first elements and the second elements, the first elements being of a same number as analyzing targets with an initial element corresponding to a first starting time point of sampling points for a first discretization of time concentration curves corresponding to the tissue on the first variation, the second elements also being of the same number as the analyzing targets with an initial element corresponding to a second starting time point of sampling points for a second discretization of a time concentration curve corresponding to blood or cerebral spinal fliud on the second variation, the second starting time point being temporally disposed after the first starting time point; and
display the information on perfusion of the blood or cerebral spinal fluid as a diagnostic aid; wherein the information on perfusion of the blood or cerebral spinal fluid includes at least one of flow, mean transit time, or volume.

8. The blood or cerebral spinal fluid analyzing apparatus of claim 7,
wherein said computer is configured to calculate time variations in values each depending on a concentration of a contrast medium as the first and second variations based on contrast image data frames.

9. The blood or cerebral spinal fluid analyzing apparatus of claim 7,
wherein said computer is configured to calculate the first and second variations based on non-contrast image data derived from said frames.

10. The blood or cerebral spinal fluid analyzing apparatus of claim 9, wherein said computer is configured to calculate the first and second variations based on the non-contrast image data corresponding to the frames acquired dynamically by changing a time from a common labeling pulse to a timing for acquiring imaging data using a magnetic resonance imaging apparatus.

11. The blood or cerebral spinal fluid analyzing apparatus of claim 9,
wherein said computer is configured to calculate the first and second variations based on the non-contrast image data corresponding to the frames acquired by repeating an application of an inversion recovery pulse or a saturation pulse and an acquisition of imaging data with changing a time from an application timing of the inversion recovery pulse or the saturation pulse to an acquisition timing of the imaging data using a magnetic resonance imaging apparatus.

12. The blood or cerebral spinal fluid analyzing apparatus of claim 9,
wherein said computer is configured to calculate the first and second variations based on the non-contrast image data corresponding to the frames acquired by repeating an application of an inversion recovery pulse or a saturation pulse and an acquisition of imaging data with changing an region for applying the inversion recovery pulse or the saturation pulse using a magnetic resonance imaging apparatus.

13. A blood or cerebral spinal fluid analyzing method comprising:
using at least one computer configured to
calculate a first variation as a first amount and a second variation as a second amount between frames of image data based on pieces of image data of an object, the first amount depending on a concentration of a pixel value at each pixel corresponding to a tissue, the second amount depending on a concentration of a pixel value corresponding to a blood or cerebral spinal fluid, the pieces of image data having been derived from the frames;
make first elements based on the first variation and second elements based on the second variation to calculate information on a perfusion of the blood or cerebral spinal fluid with deconvolution processing based on the first elements and the second elements, the first elements having a same number as analyzing targets with an initial element corresponding to a first starting time point of sampling points for a first discretization of time concentration curves corresponding to the tissue on the first variation, the second elements also having the same number as the analyzing targets with an initial element corresponding to a second starting time point of sampling points for a second discretization of a time concentration curve corresponding to blood or cerebral spinal fluid on the second variation, the second starting time point being temporally disposed after the first starting time point; and
display the information on perfusion of the blood or cerebral spinal fluid as a diagnostic aid; wherein the information on perfusion of the blood or cerebral spinal fluid includes at least one of flow, mean transit time, or volume.

14. The blood flow perfusion analyzing apparatus as in claim 1,
wherein a determinant to calculate a transfer function of said tissue is derived by making a time concentration curve corresponding to the artery discrete by setting a phase $i_{bs}$ at the head as a datum to make a data set and making time concentration curves corresponding to said tissue discrete by setting a phase corresponding to an element $P_0$ ahead of the phase $i_{bs}$ at the head, as a datum to make data sets.

15. The blood flow perfusion analyzing method as in claim 1,
wherein a determinant to calculate a transfer function of said tissue is derived by making a time concentration curve corresponding to the artery discrete by setting a phase $i_{bs}$ at the head as a datum to make a data set and making time concentration curves corresponding to said tissue discrete by setting a phase corresponding to an element $P_0$ ahead of the phase $i_{bs}$ at the head, as a datum to make data sets.

* * * * *